United States Patent [19]
Ditrich et al.

[11] Patent Number: 5,905,167
[45] Date of Patent: May 18, 1999

[54] SEPARATION OF OPTICALLY ACTIVE AMIDES

[75] Inventors: Klaus Ditrich, Gönnheim; Friedhelm Balkenhohl, Limburgerhof; Wolfgang Ladner, Fussgönheim, all of Germany

[73] Assignee: BASF Aktiengesellschaft, Ludwigshafen, Germany

[21] Appl. No.: 09/000,278

[22] PCT Filed: Sep. 9, 1996

[86] PCT No.: PCT/EP96/03948

§ 371 Date: Jan. 27, 1998

§ 102(e) Date: Jan. 27, 1998

[87] PCT Pub. No.: WO97/10201

PCT Pub. Date: Mar. 20, 1997

[30] Foreign Application Priority Data

Sep. 15, 1995 [DE] Germany .......................... 195 34 208

[51] Int. Cl.$^6$ .................................................. C07C 59/125
[52] U.S. Cl. .......................... 562/588; 564/384; 564/385; 564/424

[58] Field of Search .............................. 562/588; 564/384, 564/385, 424

[56] References Cited

U.S. PATENT DOCUMENTS 3,592,854  7/1971  Potts et al. .

FOREIGN PATENT DOCUMENTS 2170059   3/1995  Canada .
38 19 438 1/1989  Germany .
95/08636  3/1995  WIPO .

*Primary Examiner*—Paul J. Killos
*Attorney, Agent, or Firm*—Keil & Weinkauf

[57] ABSTRACT

The present invention relates to a process for cleaving optically active amides to carboxylic acids and optically active amines with retention of the center of chirality, wherein the amides are hydrolyzed in the presence of a polyol or of an amino alcohol and of an alkali metal or alkaline earth metal hydroxide.

6 Claims, No Drawings

SEPARATION OF OPTICALLY ACTIVE AMIDES

The present invention relates to a novel process for cleaving optically active amides.

The hydrolytic cleavage of optically active amides which have a center of chirality in the amine part of the molecule cannot be carried out, or can be carried out only under very elaborate conditions, to result in retention of the center of chirality.

Devant and Braun (Chem. Berichte 119 (1986) 2197–2207) describe the impossibility of eliminating chiral amines from acetamides without destruction of the center of chirality (page 2194). The authors furthermore find that numerous attempts to hydrolyze the amides with alkali or acid to the carboxylic acid and optically active amine were unsuccessful, and that only reaction with dinitrogen tetroxide as described by White (J. Am. Chem. Soc. 77 (1955) 6008) leads to the desired result. However, this reaction with $N_2O_4$ is complicated and therefore unsuitable for industrial processes.

WO 95/08636 describes an enzymatic process for the resolution of racemates of optically active amines, in which the amines are acylated enantioselectively with an ester, then the mixture of acylated amine (amide) and unreacted amine is separated and, if required, the optically active amine is liberated from the acylated amine (amide) by amide cleavage. However, no parameters for process in which the amide cleavage can be carried out are given.

It is an object of the present invention to provide, precisely in view of the efficient process described in WO 95/08636 for the resolution of racemates of amines, a low-cost process which can readily be carried out industrially for the hydrolysis of optically active amides with retention of the center of chirality.

We have found that this object is achieved by a process for cleaving optically active amides to carboxylic acids and optically active amines with retention of the center of chirality, wherein the amides are hydrolyzed in the presence of a polyol or of an amino alcohol and of an alkali metal or alkaline earth metal hydroxide.

The process according to the invention is suitable for virtually all amides which can be prepared from optically active primary or secondary amines. It is particularly suitable for amides whose amine part consists of an optically active arylalkylamine.

It takes place particularly well with primary arylalkylamines, for example those of the following structures:

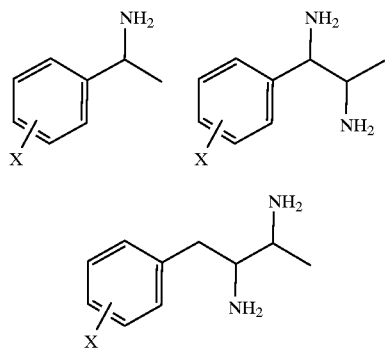

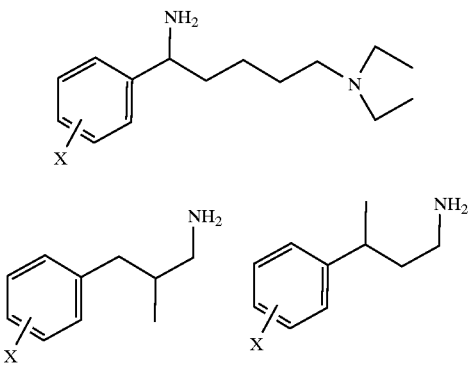

where X is any conventional aromatic substituent, in particular halogen, nitro, cyano, $C_1$–$C_4$-alkyl, $C_1$–$C_4$-alkoxy and $C_1$–$C_4$-alkylthio.

The process according to the invention is furthermore suitable for cleaving amides whose amine part consists of an amino alcohol of the general formula

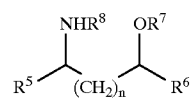

in which the substituents have the following meanings:
$R^5$, $R^6$=independently of one another H, branched and unbranched $C_1$–$C_{10}$-alkyl, $C_1$–$C_4$-alkoxycarbonyl, phenyl, phenyl-$C_1$–$C_4$-alkyl, it being possible for the phenyl groups to be substituted by halogen, nitro, cyano, $C_1$–$C_4$-alkyl, $C_1$–$C_4$-alkoxy and $C_1$–$C_4$-alkylthio. It is furthermore possible for $R^5$ and $R^6$ to be connected by a carbon chain, which can be interrupted by oxygen, sulfur or nitrogen and in turn be substituted, to form a mono-, bi- or tricyclic system
$R^7$=H, $C_1$–$C_{10}$-alkyl, $C_1$–$C_4$-alkoxycarbonyl
$R^8$=H, $C_1$–$C_{10}$-alkyl
n=0 or 1.

Where the carbon atoms substituted by $OR^7$ or $NHR^8$ are stereogenic centers, the process according to the invention relates both to the syn and to the anti isomers.

Examples of amino alcohols of the above general structure which may be mentioned are:
2-amino-1-butanol; ephedrine; pseudoephedrine; norephedrine; norpseudoephedrine; tert-leucinol; phenylglycidol; 1,2-diphenylaminoethanol; cis- and trans-2-aminocyclopentanol; cis- and trans-1-amino-2-hydroxyindane; cis- and trans-2-aminocyclohexanol, statine, 2-hydroxy-3-aminophenylpropionic acid.

Preferred amino alcohols which may be mentioned are: cis- and trans-1-amino-2-hydroxyindane.

Polyols which can be used in the process according to the invention are glycols, eg. ethylene glycol and its monoethers, eg. monomethyl glycol.

Further suitable polyols are glycerol, 1,2-propanediol, 1,3-propanediol, 1,2-butanediol, 2,3-butanediol, 2,4-pentanediol, cis- and trans-cyclohexane-1,2-diol, cis- and trans-cyclohexane-1,4-diol, 2-methyl-2,3-butanediol, 3-methyl-2,4-pentanediol, 2,2-dimethyl-1,3-propanediol, 1-phenyl-1,2-ethanediol, 3-methoxy-1,2-propanediol, 3-phenoxy-1,2-propanediol, 3-butene-1,2-diol, cis- and trans-2-butene-1,4-diol, triethanolamine, triisopropanolamine.

It is furthermore also possible to use polyalkylene glycols, preferably dialkylene glycols and their ethers, in particular diethylene glycol and diglyme, as polyols.

Suitable amino alcohols for the amide cleavage according to the invention are ethanolamine, diethanolamine and triethanolamine.

The polyols or amino alcohols should be soluble in water or homogeneously miscible with water. It is also possible to use mixtures of various polyols or amino alcohols.

Ethylene glycol is the preferred polyol.

The polyols are used in the hydrolysis in an amount of 10–90, preferably 30–80%, by weight, based on the entire solvent.

Another necessary constituent in the cleavage according to the invention comprises alkali metal or alkaline earth metal hydroxides, especially sodium and potassium hydroxides. These catalyze the hydrolysis, but are also neutralized by the acid which is produced, so that they are normally used in an amount of 1–10 equivalents based on amide.

The hydroxides can advantageously be used in the form of their aqueous solutions, because a certain water content is anyway required in the cleavage according to the invention. The water content is, as a rule, 5–90% by weight, based on the entire solvent. The cleavage according to the invention is preferably carried out at temperatures above 100° C., particularly preferably above 150° C.

A particularly suitable embodiment of the invention comprises carrying out the cleavage at a temperature high enough for the resulting reaction product (amine) to distil out with the steam and thus immediately to be removed from the reaction mixture, while the acid, which is in dissociated form under the alkaline conditions, remains in the mixture.

The process according to the invention can be used very successfully as part (step 3) of the process described in WO 95/08636 for the resolution of racemates of primary and secondary amines. This process comprises the following steps:

1. reaction of the racemic amines with an ester whose acid component has a fluorine, nitrogen, oxygen, phosphorus or sulfur atom bonded to a carbon atom in the position alpha, beta or gamma to the carbonyl carbon, with specific catalysis by a hydrolase,
2. separation of the enantioselectively acylated amine from the other, unreacted, enantiomer of the amine,
3. subsequent hydrolysis of the acylated amine.

The esters suitable for this process are those which have in the acid component of the ester an electron-rich heteroatom bonded to a carbon atom which is in the position alpha, beta or gamma to the carbonyl carbon.

The heteroatom can be a fluorine, nitrogen, oxygen, phosphorus or sulfur atom. Oxygen is preferred as heteroatom.

The heteroatom can, where appropriate, be linked to other groups, eg. alkyl groups. If the heteroatom is oxygen, for example, the compound is an ether.

The alcohol component of the ester can comprise branched or unbranched $C_1$–$C_{10}$-alcohols which may also be substituted.

Particularly suitable alcohol components are 2-propanol, 2-butanol, 2-pentanol, 3-pentanol, 3-methyl-2-butanol, cyclopentanol, cyclohexanol, 2-methylcyclohexanol, 1-chloro-2-propanol, 1-bromo-2-propanol, 4-methyl-2-pentanol, 2,4-dimethyl-3-pentanol, cyclopropylethanol, 1-phenylethanol, 1-phenoxy-2-propanol, 1-methoxy-2-propanol, cis- and trans-2-methoxycyclohexanol, 1-dimethylamino-2-propanol, 1-buten-3-ol, 1-butyn-3-ol, 1-indanol, 2-indanol, 3-hydroxytetrahydrofuran, 5-hydroxy-2-methyl-1,3-dioxane, 4-hydroxypiperidine, (+)-and (−)-menthol, (+)- and (−)-isomenthol, carfenol, lactonitrile, acetone cyanohydrin, benzaldehyde cyanohydrin, pantolactone, t-butyl lactate, acetone 2-hydroxypropyloxime.

Further suitable alcohol components are 1,2-ethanediol, glycerol, 1,2-propanediol, 1,3-propanediol, 1,2-butanediol, 2,3-butanediol, 2,4-pentanediol, cis- and trans-cyclohexane-1,2-diol, cis- and trans-cyclohexane-1,4-diol, 2-methyl-2,3-butanediol, 3-methyl-2,4-pentanediol, 2,2-dimethyl-1,3-propanediol, 1-phenyl-1,2-ethanediol, 3-methoxy-1,2-propanediol, 3-phenoxy-1,2-propanediol, 3-chloro-1,2-propanediol, 3-bromo-1,2-propanediol, 3-butene-1,2-diol, cis- and trans-2-butene-1,4-diol, triethanolamine, triisopropanolamine.

Particularly suitable esters are those with the structure

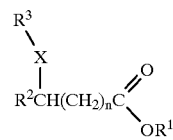

where
$R^1 = C_1$–$C_{10}$-alkyl,
$R^2 = C_1$–$C_{10}$-alkyl, H
$R^3 =$ H, $C_1$–$C_{10}$-alkyl, phenyl which is unsubstituted or substituted by $NH_2$, OH, $C_{1-4}$-alkoxy or halogen,
X = O, S, $NR^4$,
$R^4 =$ H, $C_1$–$C_{10}$-alkyl, phenyl which is unsubstituted or substituted by $NH_2$, OH, $C_{1-4}$-alkoxy or halogen,
n = 0, 1 or 2.

Among these, the $C_{1-4}$-alkyl esters of $C_{1-4}$-alkoxyacetic acids, for example of methoxyacetic acid, are preferred. The methyl, ethyl, n-propyl, i-propyl, n-butyl, i-butyl, tert-butyl esters of methoxyacetic acid are very particularly preferred.

It is possible to use a large number of enzymes as hydrolases in the said process. Proteases and, in particular, lipases are preferably used. Particularly suitable lipases are microbial lipases which can be isolated, for example, from yeasts or bacteria. Particularly suitable lipases are those from Pseudomonas, eg. Amano P or the lipase from Pseudomonas spec. DSM 8246. Further particularly suitable hydrolases are the enzymes which are commercially obtainable from Novo Nordisk (Enzyme Toolbox), especially the lipases SP 523, SP 524; SP525, SP 526 and Novozym® 435.

It is furthermore possible to use the lipases Chirazyme L1 to L8, which are commercially available (Boehringer Mannheim), advantageously in the process according to the invention.

The enzyme can be used in native or in immobilized form.

The immobilized enzyme Novozym® 435 is particularly suitable.

Solvents which are generally suitable are organic solvents. The reaction takes place particularly well in ethers, for example in MTBE or THF, or in hydrocarbons such as hexane, cyclohexane, toluene or halogenated hydrocarbons such as methylene chloride.

However, the reaction can also be carried out in the absence of a solvent.

The reaction takes place particularly well when the solvent and starting materials are as nearly anhydrous as possible.

The reaction of the ester with the racemic amine or amino alcohol with enzyme catalysis is normally carried out at room temperature. The times for this reaction depend on the substrate and are from 1 to 48 hours. Secondary amines/amino alcohols usually require longer reaction times than do primary amines/amino alcohols. The lower reactivity of secondary amines can also be compensated by a larger amount of catalyst compared with primary amines.

From 1 to 6 mol of ester are preferably added per mol of substrate to be reacted, ie. from 0.5 to 3 mol of ester are required for 1 mol of racemic amine.

The amount of enzyme to be added depends on the nature of the hydrolase and the activity of the enzyme preparation. The optimal amount of enzyme for the reaction can easily be determined by simple preliminary tests. As a rule, 1000 units of lipase are added per mmol of amine or amino alcohol.

The progress of the reaction can easily be followed by conventional methods, for example by gas chromatography. In the case of the resolution of racemates it is sensible to terminate the reaction at 50% conversion of the racemic amine or amino alcohol. This usually takes place by removing the catalyst from the reaction space, for example by filtering off the enzyme.

The enantioselective reaction of the racemic substrate with the ester results in the correspondingly acylated product (amide) from one enantiomer, while the other enantiomer remains unchanged. The mixture of amine and amide which is then present can easily be separated by conventional methods. Extraction or distillation processes, for example, are very suitable for separating the mixture of amine and amide.

The subsequent cleavage of the optically active amide takes place by the process described above.

The following examples serve to illustrate the invention.

EXAMPLE 1

Enzymatic acylation of racemic phenylethylamine

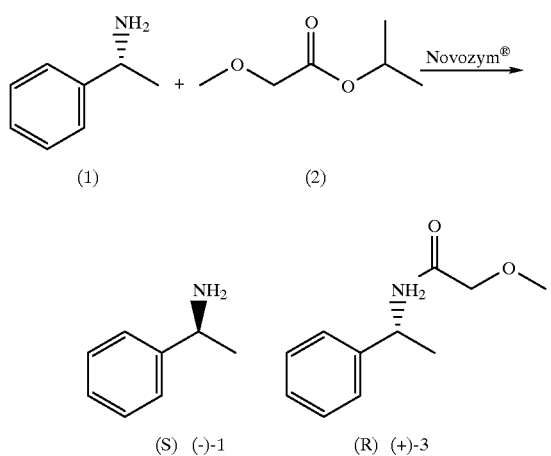

A mixture of 300 g of d,l-phenylethylamine (1) and 300 g of isopropyl methoxyacetate (2) is diluted with methyl t-butyl ether to a total volume of 1 l. This precursor solution is pumped through a continuous flow reactor packed with 50 g of Novozym® 435 at a rate such that 50% conversion is reached at the end of the reactor.

The collected product solution is freed of volatile constituents under waterpump vacuum (pressure 20 mm, temperature 35° C.). The residue is purified in a thin-film evaporator, the resulting distillate being a mixture of S-phenylethylamine (−)-1 and unreacted acylating agent (2). The residue is pure R-amide (+)-3 with melting point 63° C. (ee:>99%).

The S-amine (−)-1 can be separated from unreacted acylating agent by fractional distillation under waterpump vacuum (boiling point 73° C. under 20 mm).

This results in (−)-1 with an enantiomeric purity of >99% $[\alpha]_D = -39.5°$ (pure).

The yields of (−)-1 and (+)-3 are more than 90%.

EXAMPLE 2

Cleavage of the amide (3)

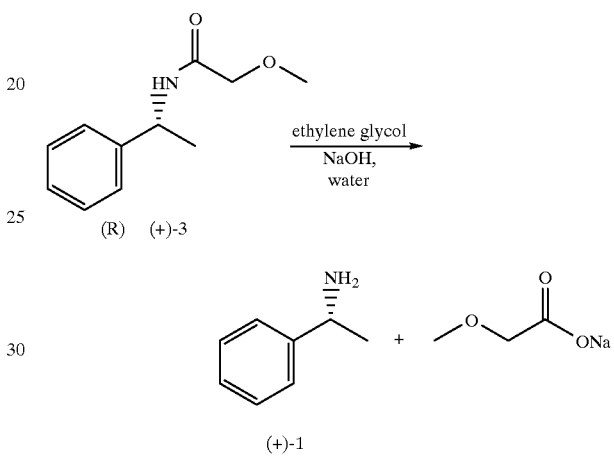

1000 g of R-amide (+)-3 from Example 1 were suspended in 1000 g of ethylene glycol and heated to 170° C., and 456 g of 50% strength aqueous sodium hydroxide solution were added in such a way that the internal temperature remained above 150° C. The liberated amine (+)-1 is distilled out as a mixture with water during this (boiling range 110–140° C.). After the addition of NaOH was complete, 750 ml of water were added dropwise to the hot mixture in order to entrain remaining product (amine) out; the phases in the distillate were then separated, the aqueous phase was extracted twice with 300 ml of toluene each time, and the combined organic phases were distilled under reduced pressure.

The aqueous phase of the distillate, which still contains about 2% amine, can be used again for entraining the amine, for example in a continuous process. The methoxyacetic acid can be recovered from the residue by acidification.

600 g (96% of theory) of R-phenylethylamine (boiling point 73° C. under 20 mm; $[\alpha]_D = 30°$ c=1.0 in ethanol with ee>99%, were obtained.

We claim:

1. A process for cleaving optically active amides to carboxylic acids and optically active amines with retention of the center of chirality, wherein the amides are hydrolyzed in the presence of a polyol or of an amino alcohol and of an alkali metal or alkaline earth metal hydroxide.

2. A process as claimed in claim 1, wherein the polyol or amino alcohol is used in the hydrolysis in an amount of from 10 to 90% by weight, based on the entire solvent.

3. A process as claimed in claim 1, wherein ethylene glycol is used as polyol.

4. A process as claimed in claim 1, wherein NaOH or KOH is employed as alkali metal hydroxide.

5. A process as claimed in claim 1, wherein the hydrolysis is carried out at a temperature above 100° C.

6. A process as claimed in claim 1 as part of a process for resolving the racemates of primary and secondary amines, which comprises the following steps:

1. reaction of the racemic amines with an ester whose acid component has a fluorine, nitrogen, oxygen, phosphorus or sulfur atom bonded to a carbon atom in the position alpha, beta or gamma to the carbonyl carbon, with specific catalysis by a hydrolase, 2. separation of the enantioselectively acylated amine from the other, unreacted, enantiomer of the amine, 3. subsequent hydrolysis of the acylated amine by one of the processes claimed above.

* * * * *